(12) United States Patent
Imhof

(10) Patent No.: US 7,631,538 B2
(45) Date of Patent: Dec. 15, 2009

(54) METHOD AND EQUIPMENT FOR MEASURING VAPOUR FLUX FROM SURFACES

(75) Inventor: Robert E. Imhof, Kent (GB)

(73) Assignee: South Bank University Enterprizes Ltd., London (GB)

( * ) Notice: Subject to any disclaimer, the term of this patent is extended or adjusted under 35 U.S.C. 154(b) by 845 days.

(21) Appl. No.: 10/535,048

(22) PCT Filed: Jan. 22, 2003

(86) PCT No.: PCT/GB03/00265

§ 371 (c)(1),
(2), (4) Date: May 5, 2006

(87) PCT Pub. No.: WO03/061462

PCT Pub. Date: Jul. 31, 2003

(65) Prior Publication Data

US 2006/0243048 A1    Nov. 2, 2006

(30) Foreign Application Priority Data

Jan. 23, 2002    (GB) ................................. 0201423.1

(51) Int. Cl.
*G01N 13/04*    (2006.01)
*G01N 25/58*    (2006.01)
*G01N 15/08*    (2006.01)

(52) U.S. Cl. .................... 73/29.01; 73/24.04; 73/25.05; 73/76; 73/335.02

(58) Field of Classification Search ............. 73/335.02, 73/335.04, 355.05, 29.01, 24.04, 73, 76
See application file for complete search history.

(56) References Cited

U.S. PATENT DOCUMENTS

| 3,521,865 | A | * | 7/1970 | Kertzman ..................... 261/95 |
| 4,050,995 | A | * | 9/1977 | Bredeweg ................... 205/788 |
| 5,752,411 | A | * | 5/1998 | Harpster .................. 73/861.04 |
| 5,826,458 | A | * | 10/1998 | Little ............................. 73/73 |
| 5,847,263 | A | * | 12/1998 | Springmann et al. ........ 73/29.01 |
| 5,907,091 | A | * | 5/1999 | Pause ............................ 73/38 |
| 6,439,028 | B1 | * | 8/2002 | Imhof ....................... 73/29.01 |

* cited by examiner

*Primary Examiner*—Hezron Williams
*Assistant Examiner*—Rodney T Frank
(74) *Attorney, Agent, or Firm*—Ronald B. Sherer; Gerow D. Brill

(57) ABSTRACT

A method and equipment for measuring vapour flux from a surface (10) e.g. the rate of water loss from human skin, which is useful in the evaluation of the efficiency of the skin/water barrier. It uses a closed cylinder (12), which is placed against the skin and by measuring the temperature and relative humidity within the cylinder by means of sensors (13, 14) positioned adjacent the wall of the cylinder, the water vapour flux can be determined.

29 Claims, 3 Drawing Sheets

METHOD AND EQUIPMENT FOR MEASURING VAPOUR FLUX FROM SURFACES

The present invention relates to a method and a device for measuring vapour flux from a surface, more particularly it relates to a method and a device which can be used to measure the rate of water loss from human skin.

The transepidermal water loss (TEWL) is important in the evaluation of the efficiency of the skin/water barrier. Damage to the skin resulting from various skin diseases, burns and other damage can affect the TEWL and measurement of the TEWL can indicate such damage and possibly its early onset or response to treatment. It therefore has use in clinical diagnosis.

As the TEWL is a measure of the effectiveness of the skin/water barrier its measurement is important in prematurely born infants, when dehydration due to excessive water loss can have serious adverse results. The TEWL is also used in testing the effect of pharmaceutical and cosmetic products applied to the skin.

GB patent 1532419 describes an instrument for measuring the rate of water loss from the skin in which an open cylinder containing two spaced apart relative humidity sensors and two temperature sensors is placed on the skin so that water vapour escaping from the skin diffuses along the cylinder and passes the sensors. The output from these sensors can be used to measure the concentration gradient of water vapour in the cylinder and hence the water vapour flux from the skin.

Patent Application WO 00/03208 describes an instrument which uses a measurement chamber in the form of a cylinder, which is open at one end and closed at the other end, in order to protect the diffusion zone from disturbance by ambient air movements. The open end is placed in contact with the surface of interest while the internal surface of the closed end is cooled to a stable and known temperature at which the water vapour in its vicinity condenses to liquid water or ice. In the absence of bulk air movements within the cylinder, the vapour entering the cylinder from the surface of interest will diffuse towards the cooled surface, where it condenses, producing a gradient of vapour density within the cylinder, parallel to its axis. The vapour flux is measured by measuring this gradient. Unlike the instrument of GB 1532419 this instrument will function with a single measurement of vapour density, typically half way between the surface of interest and the condensing surface, because the vapour density at the condensing surface itself can be calculated from its known temperature.

The method of construction of both these instruments has several drawbacks. The sensors are generally mounted close to the axis of the measurement cylinder, held in position by means of thin wires from one side of the measurement cylinder. They therefore obstruct the bore of the measurement cylinder and their physical size limits the size of the smallest bore that can be implemented. Furthermore, these sensors obstruct the path of the water vapour diffusing through the measurement cylinder, which has the effect of reducing measurement sensitivity. The construction also lacks ruggedness and makes it difficult to achieve reliable seals around the wires. Another difficulty is the positioning of the sensors in a precise and reproducible geometry, and to maintain this geometry over prolonged use, as the sensors are exposed to damage and misalignment through shock, vibration and contact with objects small enough to fit into the measurement cylinder. Also, with the sensors obstructing the bore of the measurement cylinder, cleaning of the inner wall of the measurement cylinder becomes difficult.

We have now invented an improved method and instrument.

According to the invention there is provided equipment for measuring the water vapour flux from a surface which equipment comprises a cylinder with a first end which is adapted to be placed against the surface and at least one sensor which, for vapour inside the cylinder, is able to measure the relative humidity or the relative humidity and temperature or quantities from which the flux of water vapour from the surface can be calculated, which sensor is positioned adjacent the wall of the cylinder.

Adjacent the wall of the cylinder means adjacent the inside or outside walls of the measurement cylinder and all points in between. The sensors are in contact with vapour inside the cylinder and, when the sensors are positioned inside the cylinder, they are preferably mounted in the wall, so that the sensors are as close to the wall as practical. In practice the sensors can project a small distance into the cylinder depending on the size etc. of the sensors.

When the sensor(s) is mounted on the outside of the cylinder there is preferably a hole through the wall of the cylinder, if necessary, to permit the sensor(s) or sensor combinations not mounted on the inside to be exposed to the air and water vapour within the cylinder. If the dimensions are suitable the sensor(s) can be mounted substantially or partially inside the wall in such a hole. Such a hole should be sealed against the atmosphere outside the cylinder.

Preferably the sensors are positioned about mid way between the ends of the cylinder.

In one embodiment the first end of the cylinder is placed against the surface and the second end of the cylinder is open to the atmosphere; there are two relative humidity sensors and two temperature sensors with each of said relative humidity sensors being axially spaced apart from each other and each of said temperature sensors being axially spaced apart from each other and in which the sensors are positioned adjacent the wall of the cylinder. Preferably there is a relative humidity sensor and a temperature sensor located in substantially the same place.

In use the cylinder is placed on the skin so that water vapour escaping from the skin diffuses along the cylinder and passes the sensor(s). The output from these sensors can be used to measure the concentration gradient of water vapour in the cylinder and hence the water vapour flux from the skin.

In the absence of bulk air movements within the cylinder, the vapour entering the cylinder from the surface of interest will diffuse through the cylinder and into the ambient atmosphere, producing a gradient of vapour density (or equivalently, vapour pressure) within the cylinder, parallel to its axis. The vapour flux is measured by measuring this gradient. Preferably this gradient is determined by measuring the vapour density at two positions adjacent the wall of the measurement cylinder, separated by a known distance parallel to the axis of the measurement cylinder. Vapour density at each of these positions within the measurement cylinder is conventionally and conveniently determined in such instruments by the combined readings from a relative humidity (RH) sensor and an associated temperature (T) sensor, this combination being referred to herein as an RHT sensor combination.

This embodiment of the invention also provides a method for measuring the water vapour flux from a surface, which method comprises enclosing a zone adjacent to the surface of interest within a cylinder which is open at one end and closed at the other end, by placing the open end of the cylinder against the surface of interest, cooling the surface closing the closed end of the cylinder and measuring quantities, such as relative humidity and temperature within the cylinder, from which the flux of water vapour from the surface of interest can be calculated.

In another embodiment the cylinder has a first end which is open and a second end which is closed, the first end being adapted to be placed against the surface and there being a cooling means adapted to cool the second end of the cylinder.

A suitable and convenient choice of relative humidity sensor includes sensors based on the change in capacitance or change in electrical conductivity etc, which are widely commercially available. A suitable and convenient choice of temperature sensor includes the conventional thermocouple and thermistor, which are widely commercially available. Alternatively a composite sensor can be used which simultaneously measures the relative humidity and the temperature so that one such composite sensor can produce the required signals.

An additional temperature sensor is preferably placed in contact with the cold surface in order both to maintain its temperature at a constant value and to provide a temperature reading from which the concentration of water vapour in its immediate vicinity can be calculated.

Preferably the outputs from the sensors are fed to a processing device such as a microprocessor or PC, which is programmed to convert the signals from the sensors to the required type of output or readout. By this means a user of the equipment can obtain a result in a form which requires little further processing and can be interpreted easily e.g. the flux of water vapour can be directly displayed.

The closed surface of the cylinder can be cooled by conventional cooling means and preferably uses an electrical cooling means e.g. one based on the Peltier effect. This enables the cooling to be accurately controlled at the requisite level quickly and easily.

The water which is condensed at the cold surface can be re-evaporated by heating the surface during times when the instrument is not being used for measurement. If the cooler is a Peltier device, then this can conveniently be accomplished by reversing the current flow through it.

The cylinder is the common geometry of measurement chamber for such instruments, but any convenient shape can be used e.g. rectangular parallelepiped, prism, etc. The measurement chamber is preferably made of compact size so that it occupies a small area and can easily be placed on the surface of interest, e.g. the skin at the desired location of a TEWL measurement. The measurement chamber can conveniently be constructed in the form of a wand or with a convenient handle etc.

The equipment and method can be used to measure any vapour flux from a surface although, when the vapour is not water vapour, the sensor(s) and cold plate temperature are chosen accordingly and, apart from skin, the equipment can be used to measure water vapour flux from plants, etc.

The invention relies on a distribution of vapour density within the measurement cylinder which is substantially uniform within planes perpendicular to its axis.

Therefore, any gradient of water vapour density parallel to the axis of the measurement cylinder, associated with a finite flux density of water vapour diffusing within it, will manifest itself in a similar way along any line parallel to the axis of the measurement cylinder, irrespective of radial position within its bore. Furthermore, given that the transport mechanism for the water vapour within the measurement cylinder is diffusion, the water vapour can migrate through any small holes in the side wall of the measurement cylinder, thus allowing a sensor combination to be mounted within the wall or on the outside of the measurement cylinder. If such holes are sealed beyond the position of the sensor, then there can be no net flux of water vapour migrating through them in the steady state. The vapour density gradient along the bores of such holes will therefore be zero and the vapour density sensed at any position along such bores will be the same as the vapour density at the inside wall of the measurement cylinder.

It is recognised in the above that the relative humidity and temperature within the measurement cylinder are not uniform, but change with both axial and radial co-ordinates. Therefore, the readings of any sensors located close to the axis of the measurement cylinder will generally differ from those of similar sensors with similar axial co-ordinate, but located at or within the wall of the measurement cylinder.

Despite these differences, local water vapour density values can still be calculated and the vapour flux determined by the vapour density gradient method.

It is also recognised is that the time taken for steady conditions of water vapour density along a small hole in the wall of the measurement cylinder is finite and may decrease the response speed of the instrument. The variables that affect this time are the length of the hole parallel to its axis, the diameter of the hole and the volume of any cavity in the region of the sensor(s). With careful design, this response time can be made sufficiently small for its contribution to the overall response speed of the instrument to become unimportant.

The invention is illustrated in the accompanying drawings in which

Figure 1:
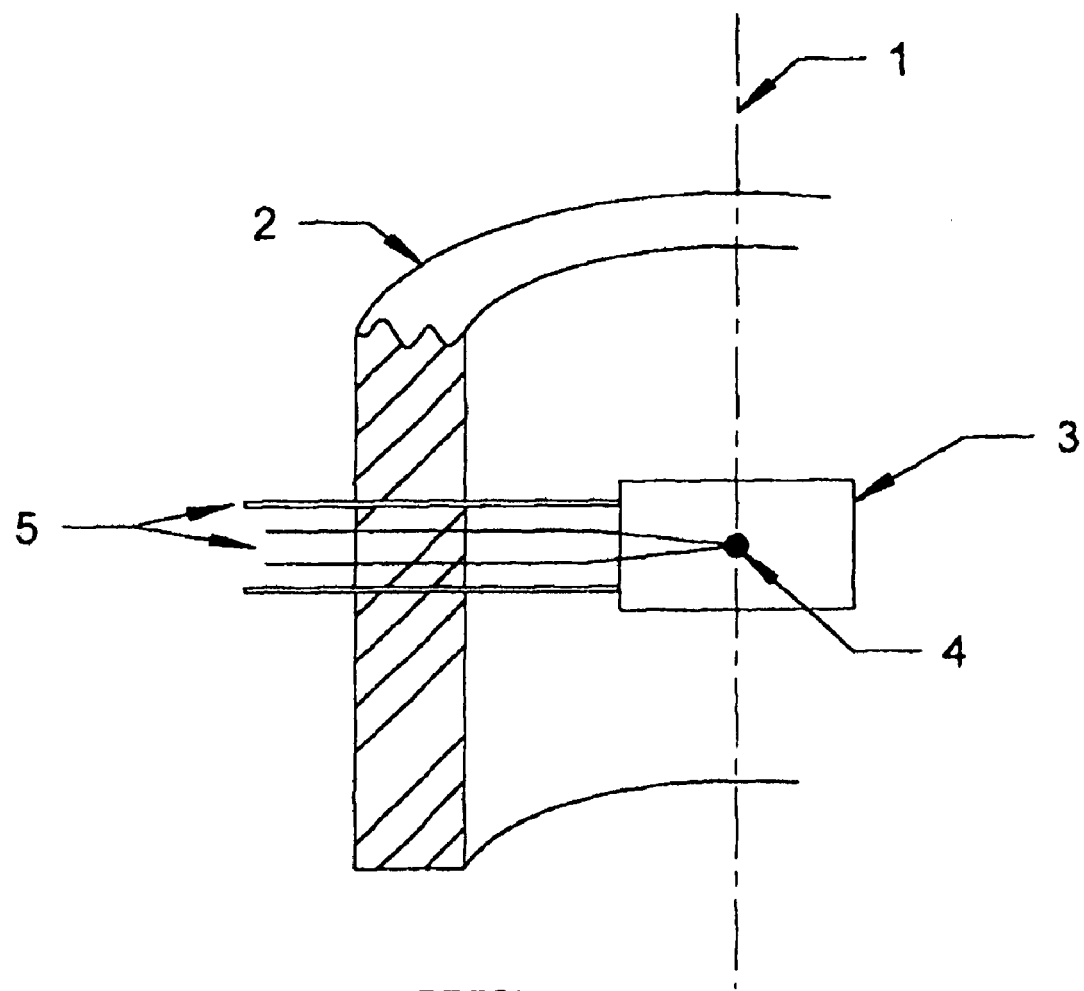
FIG. 1 is a view of a prior art device

Referring to FIG. 1 this shows part of the wall of an instrument for measuring the vapour flux from a surface. A measurement cylinder has a wall (2) and an axis shown by line (1). There is a relative humidity and temperature sensor combination, consisting of a relative humidity sensor (3) and temperature sensor (4) shown mounted close to the axis of the cylinder, supported by two pairs of wires (5), which also act to transmit the electrical signals from the individual sensors to the signal processing electronics (not shown). The sensor combination measures the relative humidity and temperature. In use to measure the water vapour flux from the skin the cylinder is placed against the skin and the closed surface (not shown) is cooled down to a sufficiently low temperature to maintain a substantially lower water vapour pressure in its immediate vicinity than in the immediate vicinity of skin at the other end of the cylinder.

A computer is programmed with a program so that the output from the sensors (3) and (4) are converted to a reading in the desired form, e.g. water vapour flux from the surface.

After a short period of time (to allow for steady state conditions to be attained inside cylinder) the readings are evaluated by the computer. Alternatively, readings can be taken continuously or periodically in order to record the time change of the signals and the water vapour flux calculated according to suitable criteria. As can be seen the sensors and the associated wires obstruct the bore of the measurement cylinder and their physical size limits the size of the smallest bore that can be implemented. Furthermore, these sensors obstruct the path of the water vapour diffusing through the measurement cylinder, which has the effect of reducing measurement sensitivity.

Figure 2:
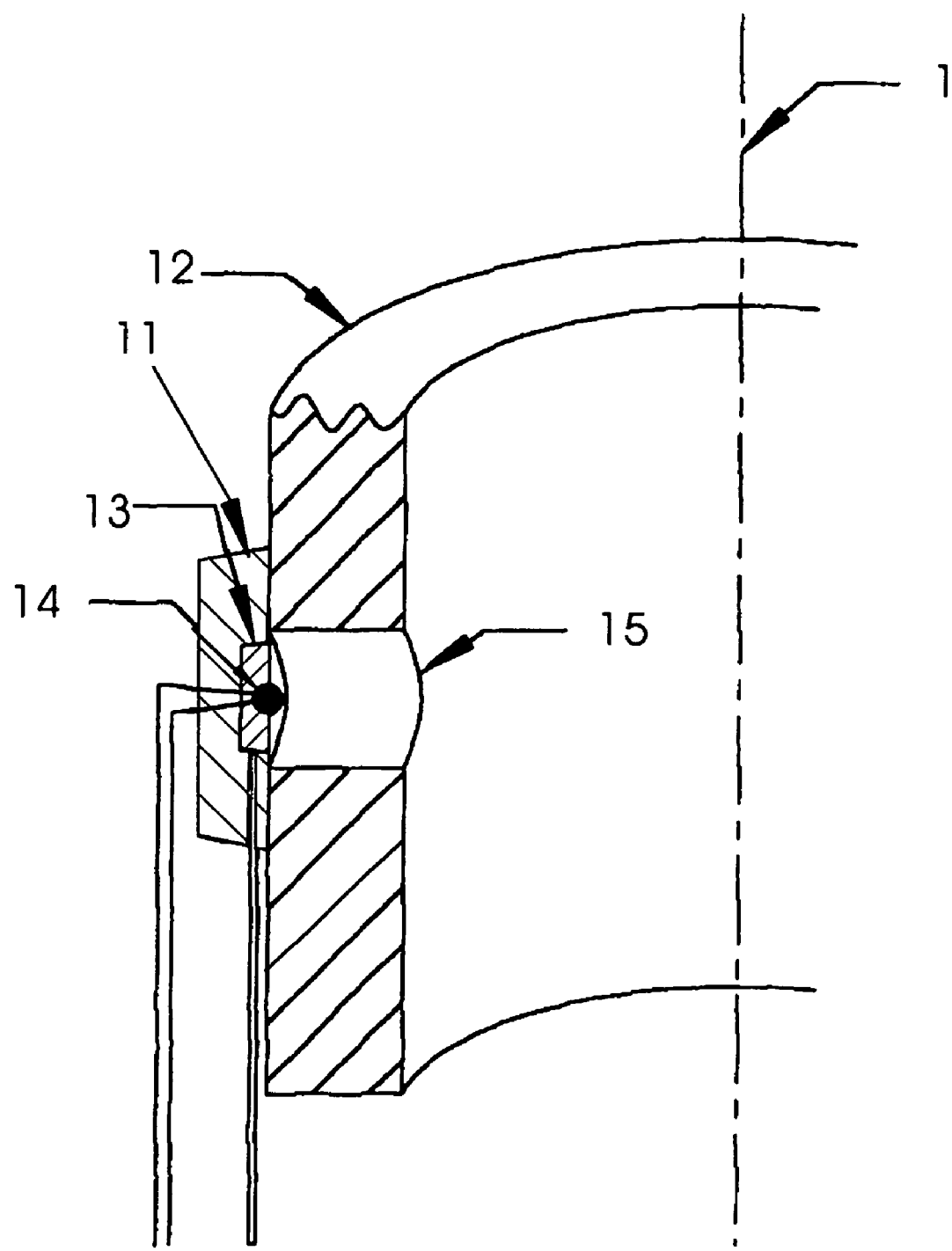
FIG. 2 is a view of a device of the invention.

Referring to FIG. 2, the axis of the cylindrical measurement chamber is shown by a line (1), and part of the wall of the cylindrical measurement chamber is shown at (12). Inside housing (11) the RHT sensor combination, consisting of a relative humidity sensor (13) and a temperature sensor (14) is shown mounted against the outer wall of the measurement cylinder in such a way as to prevent exchange of water vapour with the ambient atmosphere. A small hole (15) allows air and water vapour within the measurement cylinder to reach the sensors.

Figure 3:
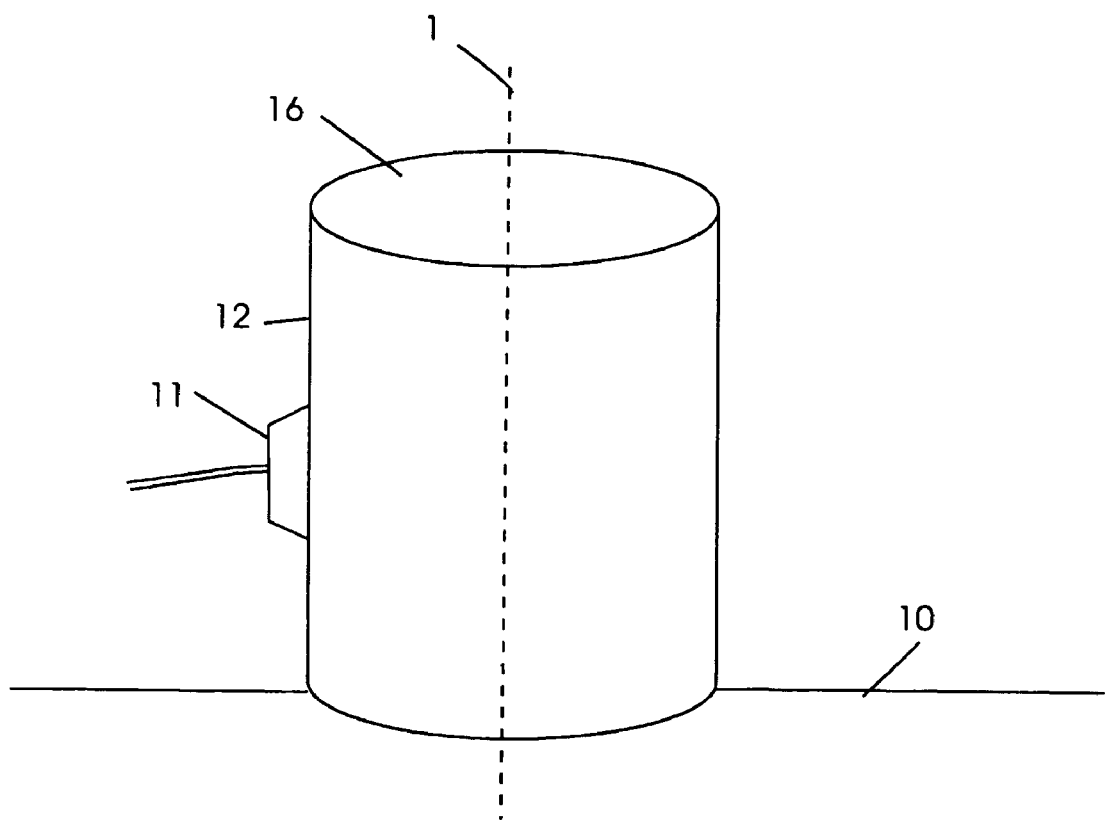
FIG. 3 shows schematically the device of FIG. 2 in position

In use, as shown in FIG. 3, to measure the water vapour flux from the skin, the cylinder (12) is placed against the skin (10) and the closed surface (16) of cylinder (12) is cooled down to a sufficiently low temperature to maintain a substantially lower water vapour pressure in its immediate vicinity than in the immediate vicinity of skin at the other end of the cylinder.

A computer is programmed with a program so that the output from the sensors (13) and (14) are converted to a reading in the desired form, e.g. water vapour flux from the surface.

After a short period of time (to allow for steady state conditions to be attained inside cylinder (12), the readings are evaluated by the computer. Alternatively, readings can be taken continuously or periodically in order to record the time change of the signals and the water vapour flux calculated according to suitable criteria. As can be seen the sensors and the associated wires do not obstruct the bore of the measurement cylinder as in the embodiment of FIG. 1 and their physical size does not affect the size of the smallest bore that can be implemented. Furthermore, these sensors cannot obstruct the path of the water vapour diffusing through the measurement cylinder, thus increasing measurement sensitivity.

The invention claimed is:

1. Equipment for measuring the water vapour flux from a surface which equipment comprises a cylinder with a first end which is adapted to be placed against the surface and at least one sensor which is able to measure the relative humidity or the relative humidity and temperature or quantities from which the flux of water vapour from the surface inside the cylinder can be calculated, which sensor is positioned adjacent a wall of the cylinder, wherein said at least one sensor is mounted on the outside of said cylinder and there is a hole through said wall of the cylinder which hole and sensors are sealed against the atmosphere outside the cylinder.

2. Equipment as claimed in claim 1 in which said at least one sensor is mounted in said wall inside the cylinder.

3. Equipment as claimed in claim 1 in which said at least one sensor is mounted on the outside of said cylinder and there is a hole through said wall of the cylinder which hole and sensors are sealed against the atmosphere outside the cylinder.

4. Equipment as claimed in claim 1 in which said at least sensor comprises two spaced apart relative humidity sensors and two temperature sensors axially spaced apart positioned adjacent the wall of the cylinder.

5. Equipment as claimed in claim 4 in which there is a first sensor able to measure the relative humidity and a second sensor which is able to measure the temperature substantially at the location of the first sensor.

6. Equipment as claimed in claim 1 in which said sensor for measuring relative humidity is based on the change in capacitance or change in electrical conductivity with change in humidity.

7. Equipment as claimed in claim 1 in which the cylinder has a first end which is open and a second end which is closed, the first end being adapted to be placed against the surface and there being a cooling means to adapted to cool the second end of the cylinder.

8. Equipment as claimed in claim 7 in which said cooling means is based on the Peltier effect.

9. Equipment as claimed in claim 1 in which said at least one sensor is a composite sensor which simultaneously measures the relative humidity and the temperature.

10. A method for measuring the water vapour flux from a surface which comprises enclosing a zone adjacent to the surface within a cylinder by placing the open end of the cylinder against the surface and measuring the relative humidity and temperature or quantities from which the flux of water vapour from the surface can be calculated by means of at least on sensor positioned adjacent the wall of the cylinder, wherein the sensors are mounted on the outside wall of the cylinder and there is a hole through the wall of the cylinder which hole and sensor are sealed against the atmosphere outside the cylinder.

11. A method as claimed in claim 10 which comprises enclosing a zone adjacent to the surface within a cylinder which is open at one end and closed at the other end of placing the open end of the cylinder against the surface cooling the closed end of the cylinder and measuring quantities from which the flux of water vapour from the surface can be calculated.

12. A method as claimed in claim 11 in which the closed end of the cylinder is cooled to a temperature at which the water vapour in its vicinity condenses to liquid water or ice and steady conditions of water vapour diffusion are established within the cylinder, with the concentration of water vapour in the immediate vicinity of the cold end of the cylinder being lower than in the immediate vicinity of the surface.

13. A method as claimed in claim 10 in which the concentration of water vapour is measured by measuring the relative humidity and the temperature simultaneously at the same location.

14. A method as claimed in claim 11 in which the closed surface of the cylinder is cooled by a cooling means based on the Peltier effect and water condensed at the closed end of the cylinder is re-evaporated by heating the surface during times when the instrument is not being used for measurement by reversing the current through the cooling means based on the Peltier effect.

15. A method as claimed in claim 10 in which the sensors are mounted in the wall inside the cylinder.

16. A method for measuring the water vapour flux from a surface which comprises enclosing a zone adjacent to the surface within a cylinder by placing the open end of the cylinder against the surface and measuring the relative humidity and temperature or quantities from which the flux of water vapour from the surface can be calculated by means of at least on sensor positioned adjacent the wall of the cylinder, wherein there is a hole through the cylinder wall and the sensors are mounted at least partially within such hole and the hole and sensor are sealed against the atmosphere outside the cylinder.

17. A method as claimed in claim 16 which comprises enclosing a zone adjacent to the surface within a cylinder which is open at one end and closed at the other end of placing the open end of the cylinder against the surface cooling the closed end of the cylinder and measuring quantities from which the flux of water vapour from the surface can be calculated.

18. A method as claimed in claim 17 in which the closed end of the cylinder is cooled to a temperature at which the water vapour in its vicinity condenses to liquid water or ice and steady conditions of water vapour diffusion are established within the cylinder, with the concentration of water vapour in the immediate vicinity of the cold end of the cylinder being lower than in the immediate vicinity of the surface.

19. A method as claimed in claim 16 in which the concentration of water vapour is measured by measuring the relative humidity and the temperature simultaneously at the same location.

20. A method as claimed in claim 17 in which the closed surface of the cylinder is cooled by a cooling means based on the Peltier effect and water condensed at the closed end of the cylinder is re-evaporated by heating the surface during times when the instrument is not being used for measurement by reversing the current through the cooling means based on the Peltier effect.

21. A method as claimed in claim 16 in which the sensors are mounted in the wall inside the cylinder.

22. Equipment for measuring the water vapour flux from a surface which equipment comprises a cylinder with a first end which is adapted to be placed against the surface and at least one sensor which is able to measure the relative humidity or the relative humidity and temperature or quantities from which the flux of water vapour from the surface inside the cylinder can be calculated, which sensor is positioned adjacent a wall of the cylinder wherein there is a hole through said cylinder wall and at least one sensor is mounted at least partially within said hole and said hole is sealed against the atmosphere outside the cylinder.

23. Equipment as claimed in claim 22 in which said at least one sensor is mounted on the outside of said cylinder and there is a hole through said wall of the cylinder which hole and sensors are sealed against the atmosphere outside the cylinder.

24. Equipment as claimed in claim 23 in which said at least sensor comprises two spaced apart relative humidity sensors and two temperature sensors axially spaced apart positioned adjacent the wall of the cylinder.

25. Equipment as claimed in claim 22 in which there is a first sensor able to measure the relative humidity and a second sensor which is able to measure the temperature substantially at the location of the first sensor.

26. Equipment as claimed in claim 22 in which said sensor for measuring relative humidity is based on the change in capacitance or change in electrical conductivity with change in humidity.

27. Equipment as claimed in claim 22 in which the cylinder has a first end which is open and a second end which is closed, the first end being adapted to be placed against the surface and there being a cooling means to adapted to cool the second end of the cylinder.

28. Equipment as claimed in claim 26 in which said cooling means is based on the Peltier effect.

29. Equipment as claimed in claim 22 in which said at least one sensor is a composite sensor which simultaneously measures the relative humidity and the temperature.

* * * * *